(12) United States Patent
Baker et al.

(10) Patent No.: US 6,689,354 B2
(45) Date of Patent: *Feb. 10, 2004

(54) IMMUNOGENIC PREPARATION AND METHOD FOR IMPROVING THE PRODUCTIVITY OF RUMINANT ANIMALS

(75) Inventors: Suzanne Kay Baker, Wembley Downs (AU); Gnanapragasam Gnanasampanthan, Bateman (AU); Douglas Barrie Purser, Wembley Downs (AU); Ronald Milton Hoskinson, Prospect (AU)

(73) Assignee: Commonwealth Scientific and Industrial Research Organization, Campbell (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/147,371
(22) PCT Filed: Jun. 14, 1996
(86) PCT No.: PCT/AU96/00356
§ 371 (c)(1),
(2), (4) Date: Feb. 5, 1999
(87) PCT Pub. No.: WO97/00086
PCT Pub. Date: Jan. 3, 1997

(65) Prior Publication Data
US 2002/0034523 A1 Mar. 21, 2002

(30) Foreign Application Priority Data
Jun. 14, 1995 (AU) .............................. PN 3536

(51) Int. Cl.[7] .................. A61K 39/00; A61K 39/02; A01N 63/00; A01N 37/18
(52) U.S. Cl. ................ 424/93.1; 424/184.1; 424/234.1; 514/2
(58) Field of Search .................. 435/325, 252.1; 530/300, 350, 351, 412; 424/130.1, 184.1, 93.1, 234.1; 514/2.21, 2

(56) References Cited

U.S. PATENT DOCUMENTS 5,512,288 A * 4/1996 Olson et al. ............. 424/269.1
6,036,950 A * 3/2000 Baker ....................... 424/93.1

FOREIGN PATENT DOCUMENTS

EP 0159054 10/1985

OTHER PUBLICATIONS

Krumholz, Can. J. Microbiol, 29:676–80, 1983.*
Barrett, Textbook of Immunology, CV Mosby Co., 1983.*
Abstract Coleman et al, Techniques for the study of mixed populations, Soc. for Applied Bacteriol. Tech. Series No. 11, pp. 143–163, 1978.*
Abstract, Kurihara, J. Agric. Sci, 1978:90(2), 373–82, 1978.*
Abstract, FEMS Microbiol. Lttrs, 1994, vol. 117(2):157–61, 1994.*
Porter et al, CIBA Foundation Symposium, 1977, Apr. 26–28, vol. 46, pp. 55–75, 1977.*
Sato et al, Jpn. J. Vet. Sci., 1990 52(4):719–26, 1990.*
Abstract, Ogimoto, Jpn. J. Zootech Sci, 54(1):33–38, 1983.*
Husband et al., Vet. Immunol. & Immunopathol. 17(1–4):357–65, 1987.*
Protoplasma 182, Sghir et al, "A 43 kDa protein inserted at the plasma membrane–cytoskeleton . . . ", pp. 149–159, 1994.
J. Gen. Appl. Microbiol. 41, Takenaka et al, "Changes in the Population of Some . . . ", pp. 377–387, 1995.
Can. J. Microbiol., vol. 29, Krumholz et al, "Association of methanogenic bacteria . . . ", pp. 676–680, 1983.
FEMS Microbiol. Ltrs. 117, Ellis et al, "Polypeptides of hydrogenosome–enriched fractions . . . ", pp. 211–216, 1994.
Dept. of Agricultural Chemistry, Hino, "Influence of Hydrogen on the Fermentation in Rumen . . . ", pp. 320–328, 1983.

* cited by examiner

Primary Examiner—John Ulm
Assistant Examiner—Olga N. Chernyshev
(74) Attorney, Agent, or Firm—Jacobson Holman PLLC

(57) ABSTRACT

A method of improving the productivity of a ruminant animal comprising administering to said animal an amount of an immunogenic preparation effective to invoke an immune response to at least one rumen protozoan, such that the immune response invoked at least reduces and preferably totally removes the activity of the at least one rumen protozoan. The invention also provides novel immunogenic preparations which may be used in the method of the invention.

17 Claims, 15 Drawing Sheets

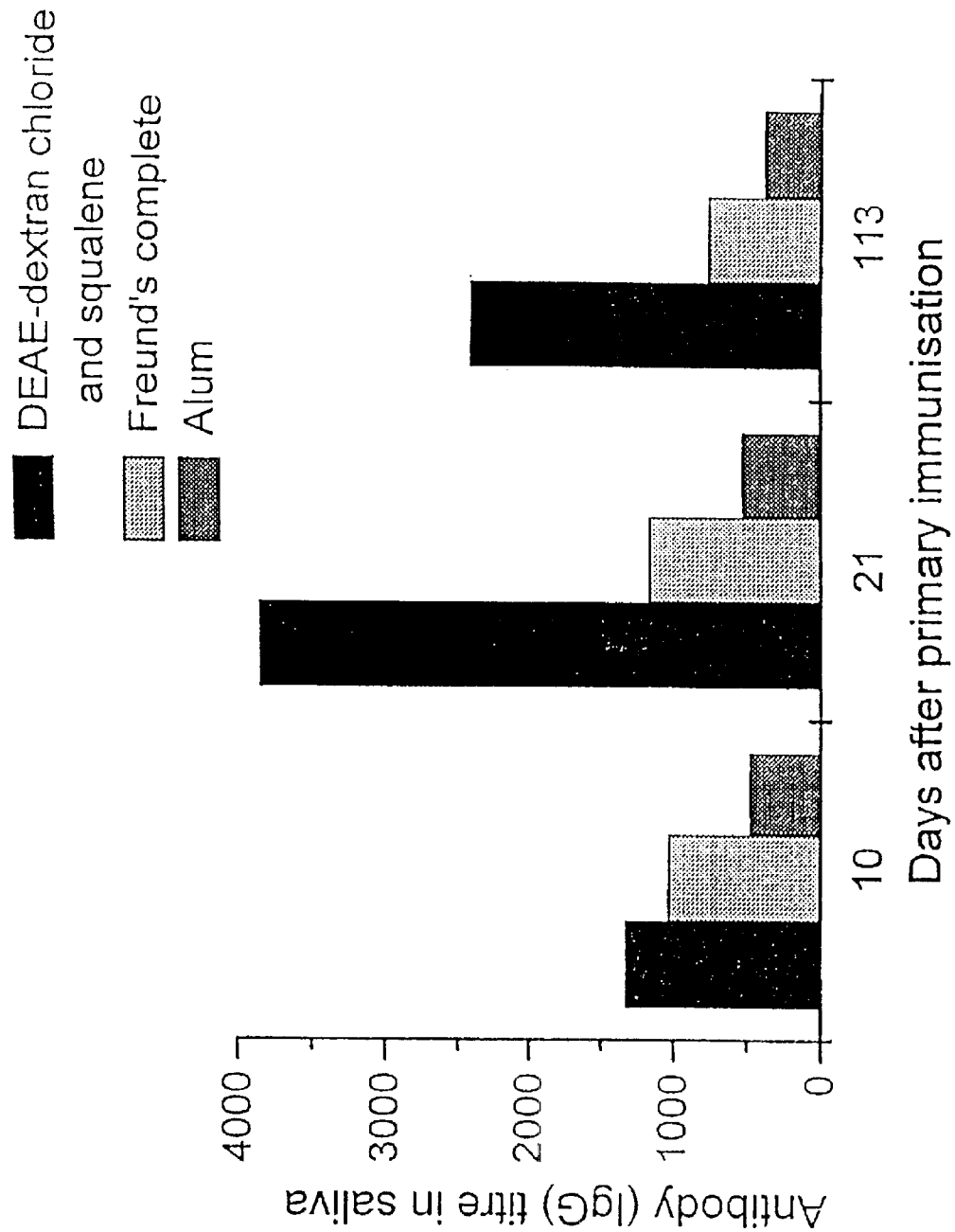

FIG. 1E

Number of animals in each treatment group of 8 animals to show a response in titre of IgG relative to preimmune saliva or serum.

| Adjuvant | DEAE dextran chloride and squalene | Freund's complete | Alum |
|---|---|---|---|
| Saliva | | | |
| Day 10 | 6/8 | 4/8 | 4/8 |
| Day 21 | 7/8 | 4/8 | 4/8 |
| Day 113 | 6/8 | 3/8 | 4/8 |
| Serum | | | |
| Day 10 | 8/8 | 5/8 | 5/8 |
| Day 21 | 8/8 | 5/8 | 2/8 |
| Day 113 | 8/8 | 6/8 | 3/8 |

FIG. 1F

NUMBER OF ANIMALS IN EACH TREATMENT GROUP OF 8 ANIMALS TO SHOW A RESPONSE IN TITRE OF IgG RELATIVE TO PREIMMUNE SALIVA OR SERUM.

|  | DEAE dextran chloride and squalene | Alum | Freund's complete |
|---|---|---|---|
| Saliva |  |  |  |
| Day 10 | 6/8 | 6/8 | 7/8 |
| Day 21 | 3/8 | 6/8 | 6/8 |
| Day 113 | 3/8 | 4/8 | 3/8 |
| Serum |  |  |  |
| Day 10 | 8/8 | 6/8 | 7/8 |
| Day 21 | 8/8 | 6/8 | 6/8 |
| Day 113 | 8/8 | 5/8 | 7/8 |

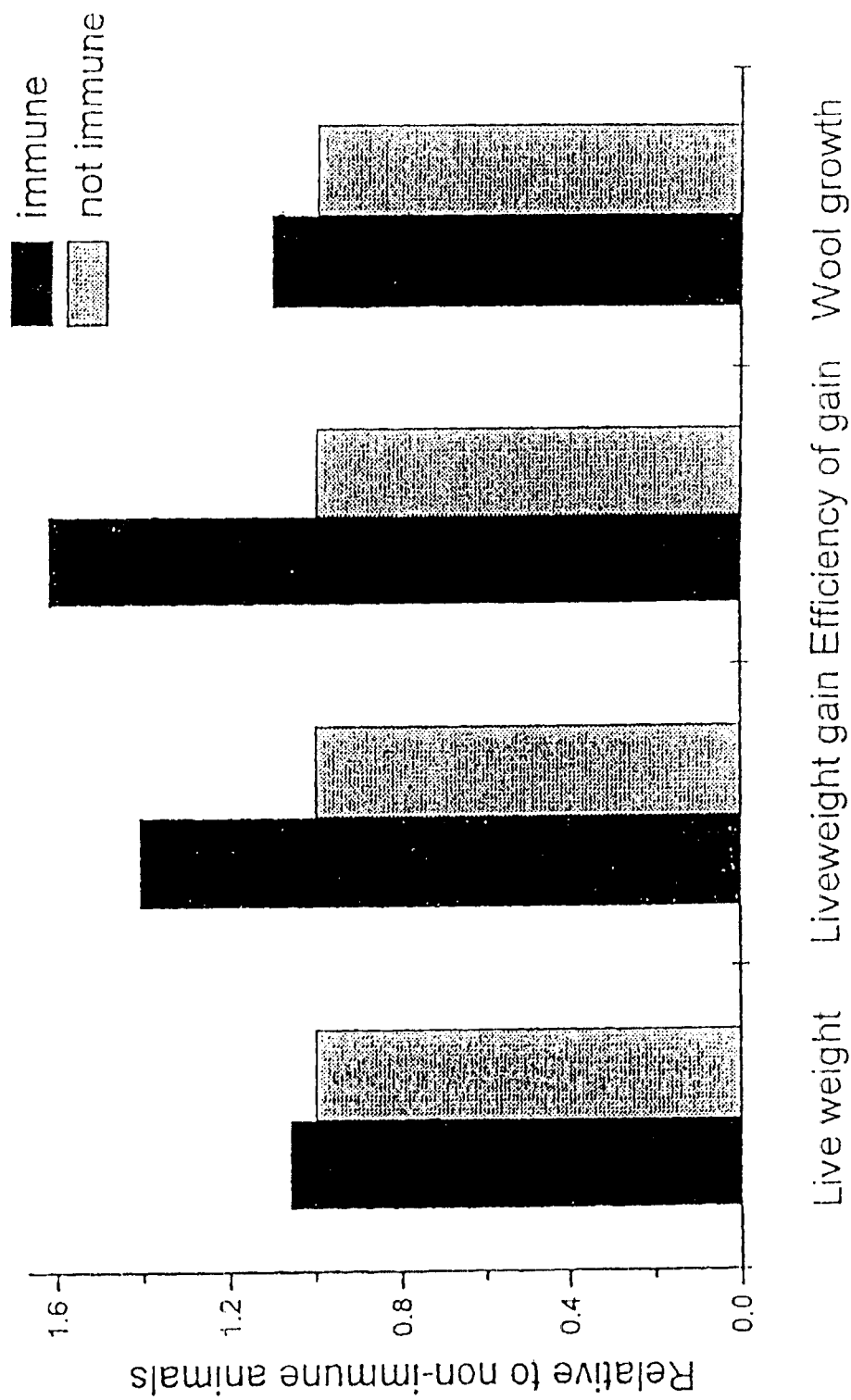

*p<0.10, p<0.01, *p<0.001

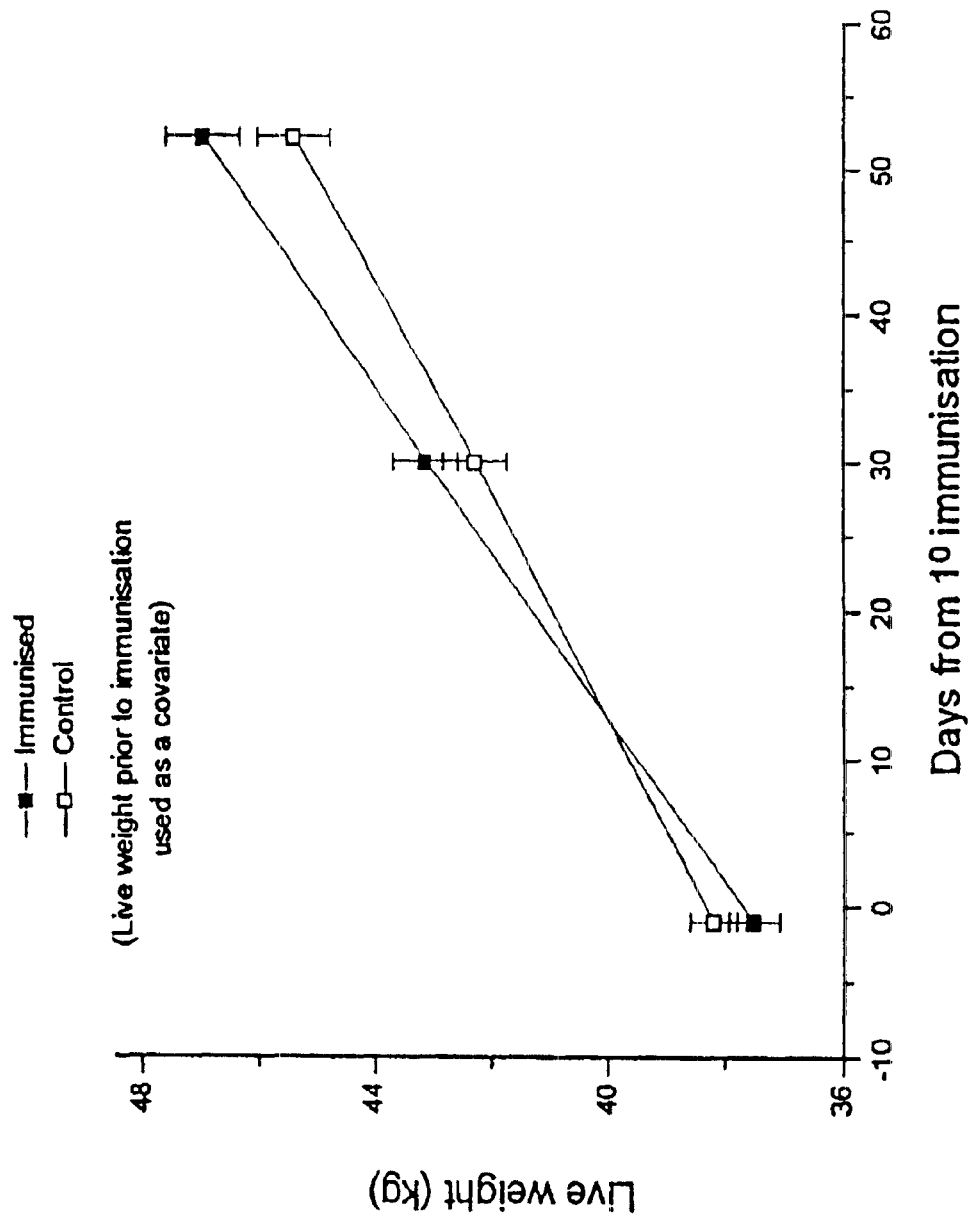

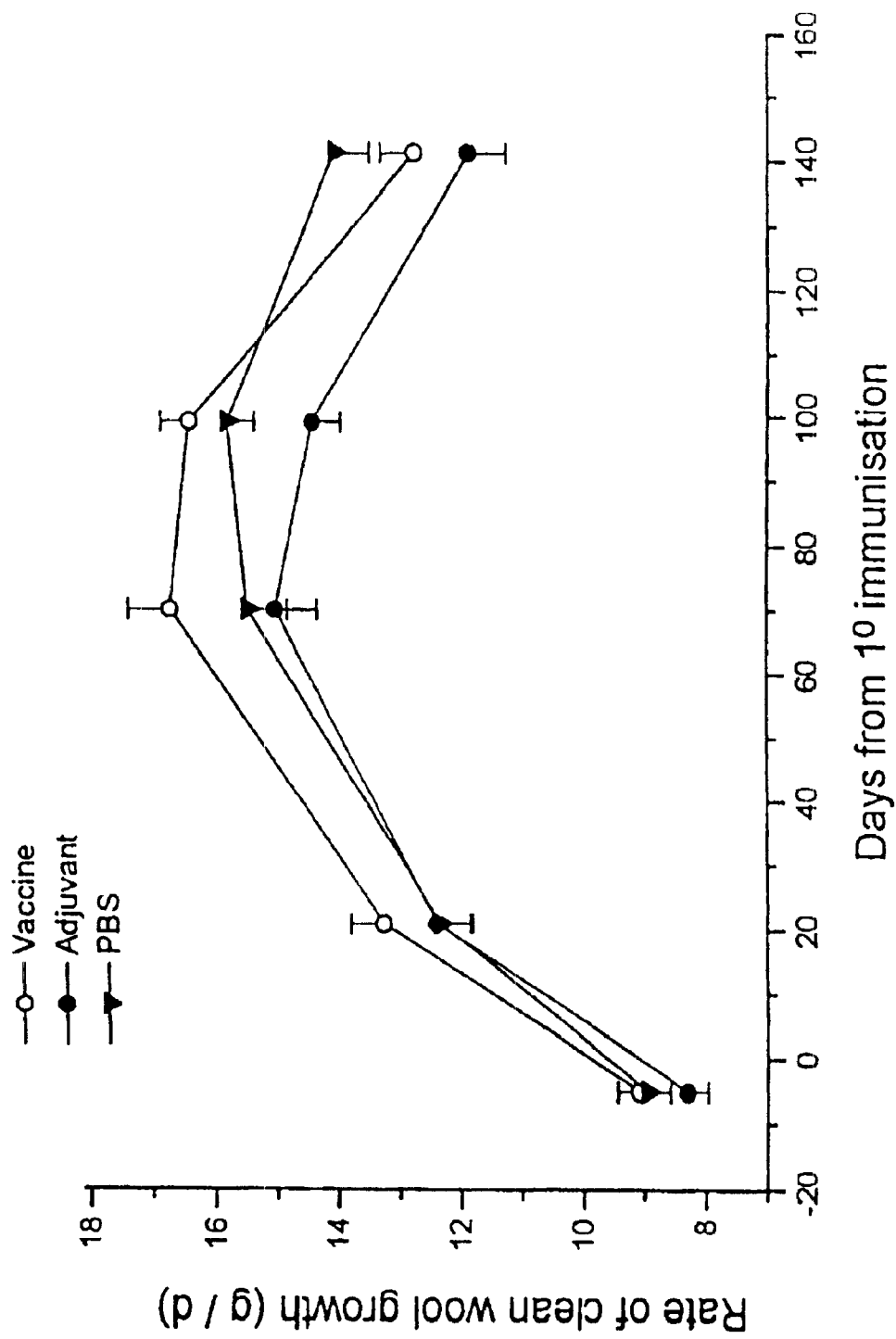

IMMUNOGENIC PREPARATION AND METHOD FOR IMPROVING THE PRODUCTIVITY OF RUMINANT ANIMALS

The present invention relates to a method of improving the productivity of a ruminant or ruminant-like animal and more particularly to a method of improving the productivity of ruminant or ruminant-like animals utilising an immunogenic preparation.

It is well known that micro-organisms in the rumen play a major role in determining the availability of nutrients to an animal. Under certain nutritional conditions the activities of some of the micro-organisms in the rumen including protozoa can seriously reduce the productivity of the animal to be significantly less than its potential.

Experimentally, it has been shown that in certain situations, removal of the protozoa from the rumen, or at least decreasing the activities of protozoa in the rumen, can result in an improvement in the ratio of protein to energy of the nutrients available for absorption from the gastro-intestinal tract of a ruminant animal. The improved nutrient availability results in an improvement in the productivity of the animal which can be measured in a variety of ways such as liveweight gain, improved milk production, improved efficiency of utilisation of feed and improved wool growth (sheep).

The present invention is based on the use of certain immunogenic preparations which have been found to be effective in altering the activities of rumen protozoa. Throughout the specification the term "ruminant animals" should be understood to include "ruminant-like animals". Furthermore, where reference is made to a "rumen" it will be understood that the term is being used so as to include the paunch of an animal classified as a ruminant-like animal.

Thus, the present invention provides a method of improving the productivity of a ruminant animal, the method comprising administering to said animal an amount of an immunogenic preparation effective to invoke an immune response to at least one rumen protozoan, the immune response invoked being effective in reducing and preferably totally removing the activity of the at least one rumen protozoan.

The immunogenic preparation employed in the method may be of various forms provided it invokes the appropriate immune response in the recipient. Preferably, the immunogenic preparation comprises an antigen preparation such as a vaccine comprising at least one antigen effective in invoking an immune response to at least one rumen protozoan. In this preferred form, the antigen preparation preferably comprises an antigen prepared from a washed preparation of at least one rumen protozoan and even more preferably the antigen preparation comprises a mixture of antigens, the antigens preferably being from a plurality of different species of rumen protozoa.

The rumen protozoa include a range of protozoa. However, preferably the at least one rumen protozoan is a member of the order Prostomatida, Trichostomatida or Entodiniomorphida. In one particularly preferred form, the at least one rumen protozoan is selected from the group of genera comprising; Diploplastron, Eodinium, Polyplastron, Entodinium, Dasytrichia and Isotrichia.

The rumen protozoa outlined above may be isolated from whole rumen contents by centrifugal elutriation. Preferably, and in the case of a sheep or another similar sized animal, the rumen protozoa have an approximate cell size between 10 and 100 $\mu$m measured as diameter of a sphere of the same volume as the cell. In the case of rumen protozoa isolated from larger animals such as cattle the approximate size of the cells may be larger than the range outlined above. Thus, in a preferred form the immunogenic preparation used in the method of the present invention may comprise antigens obtained from rumen protozoa having an approximate cell size between 10 and 100 $\mu$m. Alternatively the rumen protozoa may have an approximate cells size of between 5 and 200 $\mu$m.

Additionally, or alternatively, the immunogenic preparation may comprise an immunogenic fraction(s), polypeptide(s)/peptide(s), polysaccharide(s), or lipopolysaccharide(s) derived from one or more rumen protozoa.

The immunogenic preparation may further comprise one or more adjuvants. The one or more adjuvants may be of various forms provided they act to improve the immune response invoked in the recipient. Preferably, the adjuvant comprises a DEAE-dextran based adjuvant and in one particularly preferred form the adjuvant comprises DEAE-dextran chloride. Alternatively, the adjuvant may be selected from the group comprising; Freund's complete adjuvant (FCA), Freund's incomplete adjuvant (FIA) and alum.

The ratio of the components of the immunogenic preparation may be varied according to preference and the mode of use to which the preparation is being put. For example, an immunogenic preparation for use on weaner wethers may comprise 20 mL of the antigen preparation ($10^6$ protozoa/mL), 20 mL of 20% (w/v in PBS) diethylaminoethyl (DEAE)—dextran chloride, 1 mL of 30% (v/v in PBS) glycerol, 1 mL of 1% (v/v in PBS) Tween 80 and 35 mL squalene. When using an immunogenic preparation of this form on weaner wethers a dose of 5 mL per animal has been found to be effective.

The method of the invention makes it possible for animals to have an improved productivity. In this respect, and as will be illustrated by the examples below, animals to which the method is applied show improved characteristics such as greater liveweight, liveweight gain, improved milk production, improved efficiency of gain and improved wool growth (for sheep). These aspects of improved productivity are improvements over the normal characteristics of those animals when not subjected to the method of the invention.

It is believed that the method of invention makes it possible to increase the ratio of protein to energy available for the animal for absorption in the gastro-intestinal tract by controlling rumen protozoa. It is envisaged that the control of the rumen protozoa occurs via a reduction in the number of rumen protozoa, and/or a reduction in the activity of rumen protozoa.

As protozoa are naturally present in the rumen of the vast majority of ruminant animals, it will be appreciated that animals exposed to the invention are thus considered healthy animals and actually represent the normal population of any given animal species.

Thus, otherwise healthy animals are able to be subjected to a method of the invention so that they have an improved productivity from a more efficient utilisation of ingested nutrients and/or enhanced intake of feed. For example, animals subjected to the method of the invention may be able to meet their normal dietary requirements from a reduced amount of food or from a food supply of reduced quality.

It is also believed that by modifying the activity of the rumen protozoa there is also an indirect effect on the activity of other micro-organisms in the rumen such as methane producing bacteria. In this respect, it is noted that some methane producing bacteria in the rumen appear to have a commensal relationship with the rumen protozoa. As such by modifying the activity of the rumen protozoa there may also be a corresponding effect on the production of methane.

It is envisaged that an immunogenic preparation such as a vaccine incorporating antigens from both methanogenic bacteria, in particular those classified as archae, and protozoa may be particularly effective in achieving the method of the present invention. Thus, the immunogenic preparation of the present invention may further comprise at least one antigen from at least one methanogenic bacterium. Preferably, the methanogenic bacterium comprise bacteria, classified as archae, from the rumen. Indeed, it will be appreciated that methanogenic bacteria are present in the rumen and some may be closely associated with the rumen protozoa. Thus, when the immunogenic preparation of the present invention is prepared from whole rumen contents (incorporating methanogenic bacteria) the improved productivity of the animal subjected to the method of the invention may be enhanced when an immune response is elicited against both the methanogenic rumen bacteria and the rumen protozoa.

The present invention will now be described by way of example in relation to the following examples. The examples illustrate various aspects of the present invention, but are in no way intended to limit the scope of the preceding description. In Examples 1 and 2 FIGS. 1C, 1D and 1F illustrate results after statistical analysis to remove data having a studentized residual of greater than three (ie approximately more than three standard deviations from the mean).

EXAMPLE 1

Immunoglobulin Titres and Responses in Sheep After the Intra-peritoneal Administration of an Antigen/Adjuvant Vaccine An experiment was conducted using three test groups of eight (8) weaner wethers. Three vaccines were prepared, each using antigen prepared from a washed preparation of mixed rumen protozoa and administered to a separate test group. The mixed rumen protozoa were separated from whole rumen contents by incubating rumen fluid strained through nylon gauze in a separating funnel and allowing the protozoa to sediment. The sediment containing the protozoa was collected and the protozoa pelleted by centrifugation. The pellet was washed with and resuspended in PBS (10 mM pH 7.4.) and included protozoa belonging to a number of genera including; Diploplastron, Eodinium, Polyplastron, Entodinium, Dasytrichia and Isotrichia.

Frozen whole cells in PBS were thawed and 20 mL fractions ($10^6$ cells/mL) were incorporated into three vaccines as follows:

(i) Freund's vaccine comprising 20 mL of the antigen preparation emulsified with 20 mL of Freund's Complete Adjuvant (FCA). The dose administered was 3 mL per animal;

(ii) Alum vaccine comprising 20 mL of the antigen preparation incorporated with 10 mL of "Alhydrogel" (Superfos, Denmark) according to the manufacturer's directions. The dose administered was 2.5 mL per animal; and (iii) DEAE-dextran chloride vaccine comprising 20 mL of the antigen preparation, 20 mL of 20% (w/v in 10 mM PBS) diethylaminoethyl (DEAE)-dextran chloride, 1 mL of 30% (v/v in 10 mM PBS) glycerol, 1 mL of 1% (v/v in 10 mM PBS) Tween 80 and 35 mL squalene mixed together. The mix formed an emulsion containing oil droplets no larger than 40 $\mu$m in diameter. The dose administered was 5 mL per animal.

Each vaccine (i), (ii) and (iii) was administered intraperitoneally at the sub-lumbar fossa on the right mid-flank of the animal for the primary inoculation. The booster inoculation in each case comprised a volume of the antigen preparation plus an equal volume of sterile PBS, being 1.5 mL administered subcutaneously 80 days after the primary inoculation.

A titre of antibody (IgG) was measured in both serum and saliva obtained from each animal on days 10, 21 and 113 after primary inoculation.

FIGS. 1A and 1C illustrate the significantly potentiated and sustained IgG levels (titre) in saliva obtained from animals administered the DEAE-dextran chloride vaccine (iii) and showing an immune response at each of the 10, 21 and 113 day samples compared with those of animals administered either vaccines (i) or (ii) and showing an immune response.

FIGS. 1E and 1F are tables showing the number of animals in each test group of eight that showed an immune response. It will be noted that a greater number of animals that received the immunogenic preparation incorporating DEAE-dextran chloride as the adjuvant showed high titres of IgG that were sustained for longer compared to preparations incorporating Freund's adjuvant or alum.

FIGS. 1C, 1D and 1F are further representations of the data illustrated in FIGS. 1A, 1B and 1E after statistical analysis. It will be noted that the trends illustrated in FIGS. 1A, 1B and 1E are conserved in FIGS. 1C, 1D, and 1F.

EXAMPLE 2

Figure 1B:
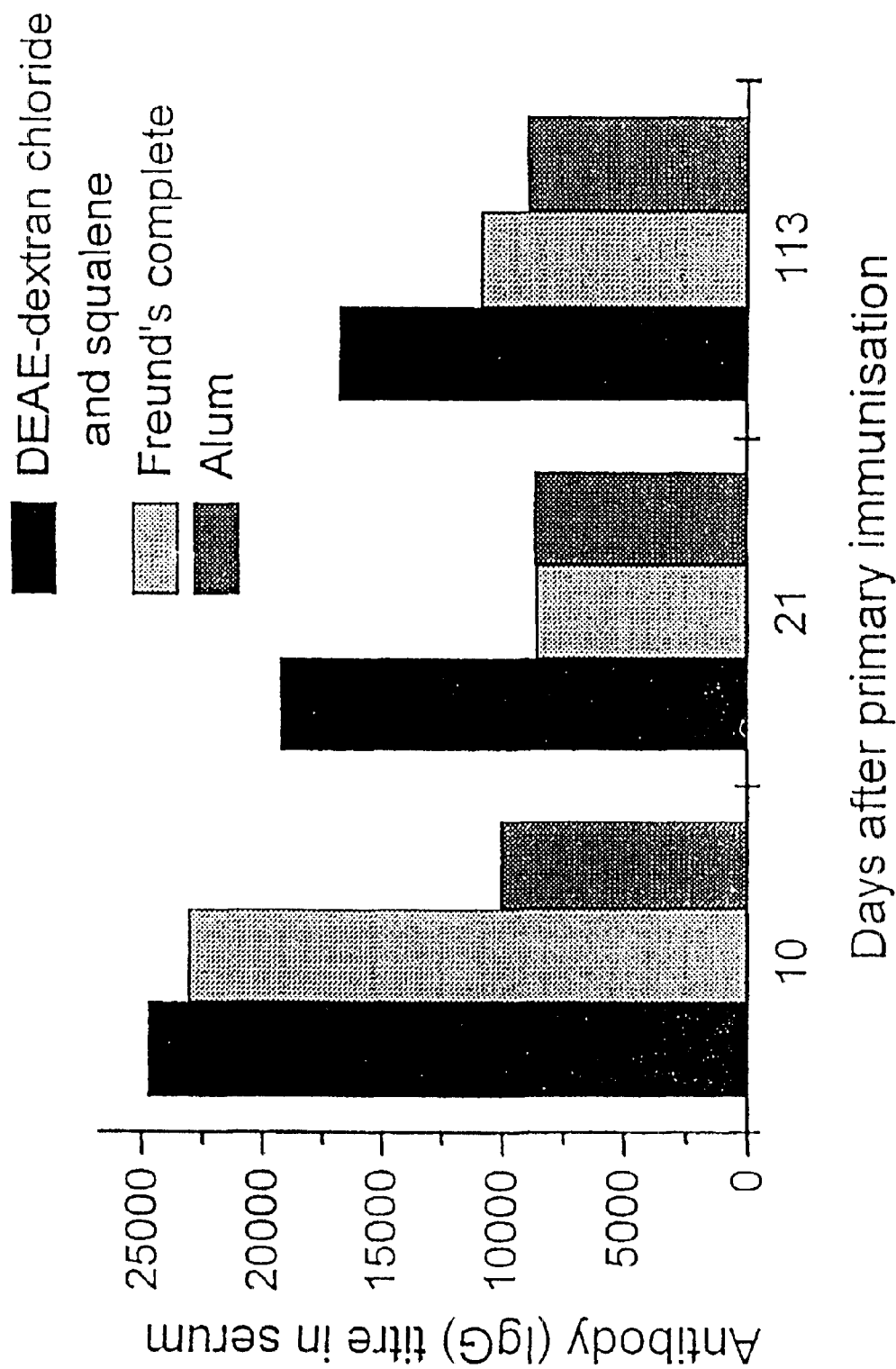
FIGS. 1B and 1D illustrate the significantly potentiated IgG levels (titre) in serum obtained from animals administered with the DEAE-dextran chloride vaccine at each of the 10, 21 and 113 day samples compared with those of animals administered either vaccines (i) or (ii) and showing an immune response.
Figure 1C:
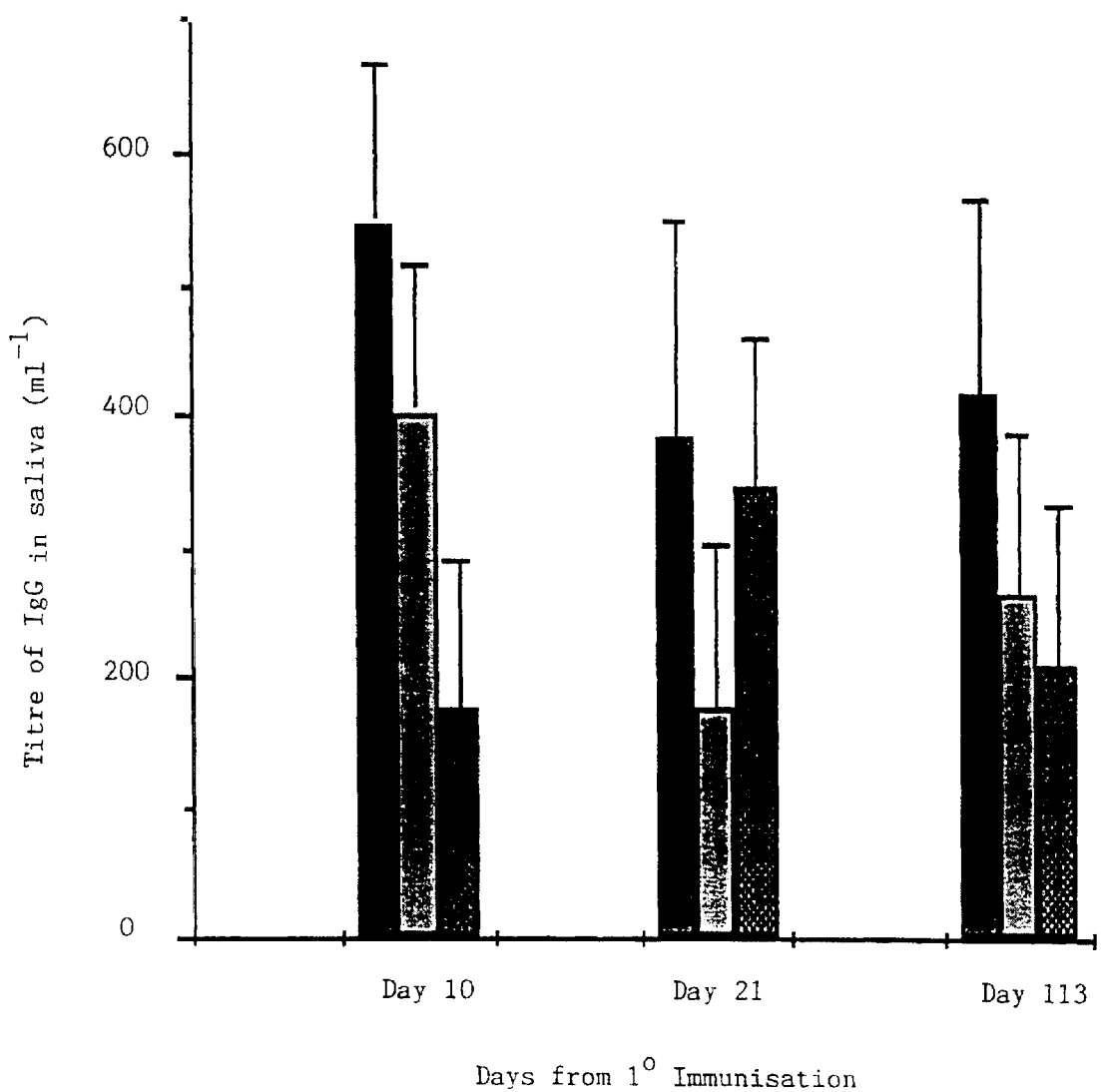
Figure 1D:
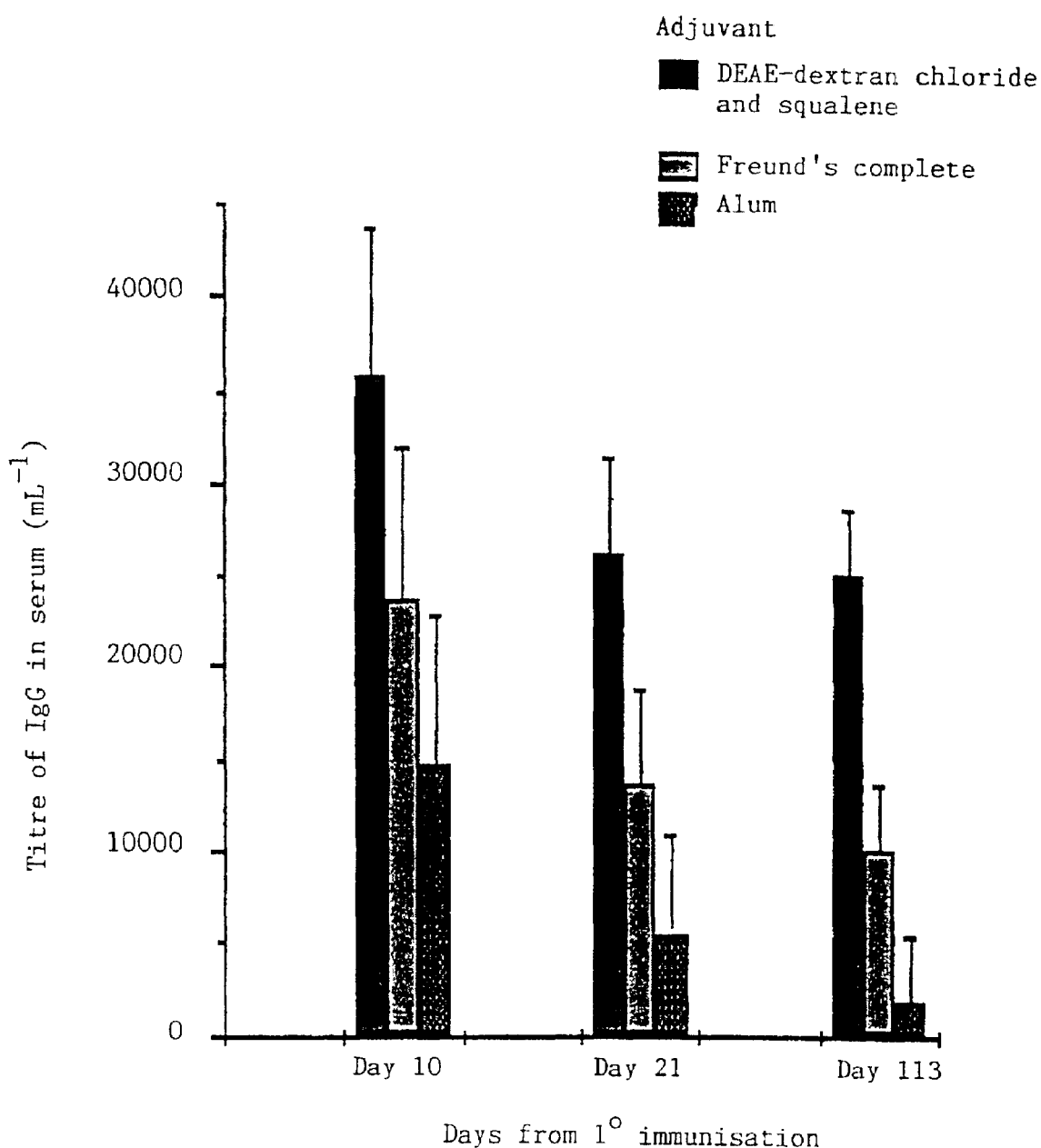

Responses in Sheep After the Administration of an Antigen/Adjuvant Vaccine

The experiment was conducted using weaner wethers (Border-Leister×Merino cross). There were 12 weaners per treatment group. The treatment groups were Group I vaccine (antigen plus adjuvant)

Group II phosphate-buffered saline (PBS) alone (control)\

The vaccine was prepared using an antigen prepared from a washed preparation of mixed rumen protozoa separated from whole rumen contents by filtration through cotton wool. A suspension of whole protozoal cells in phosphate-buffered saline (PBS) ($3 \times 10^5$ cells/mL PBS), frozen and then thawed just prior to incorporation into the vaccine was combined with Freund's complete adjuvant (FCA) as follows:

75 mL of the antigen preparation (the suspension of protozoal cells) and 75 mL of FCA were mixed together. The dose administered was 10 mL per animal. The vaccine was administered intraperitoneally to the animals in Group I at the sublumbar fossa on the right mid-flank of the animal for the primary inoculation. The booster inoculation (10 mL) comprised $1.5 \times 10^5$ protozoal cells/mL in PBS (10 mM PBS adjusted to pH 7.2) and was administered intramuscularly to the animals in Group I, 28 days after the primary inoculation.

The animals in Group II received 10 mL of 10 mM PBS (adjusted to pH 7.2) at the same times and by the same routes of inoculation as the animals in Group I received the vaccine and booster inoculation.

The sheep were housed in indoor pens, and given a ration (1500 g air-dry/d) once daily of pelleted mixture supplied by Australian Feed Services Pty Ltd, Adelaide, South Australia which comprised (g air-dry ingredient per kg of feed mixture) oat hulls (400), oat grain (390), triticale (150), bentonite (20), salt (10), limestone (20), urea (5), and vitamins and minerals (10). Oaten straw was available to the animals ad libitum.

Figure 2B:
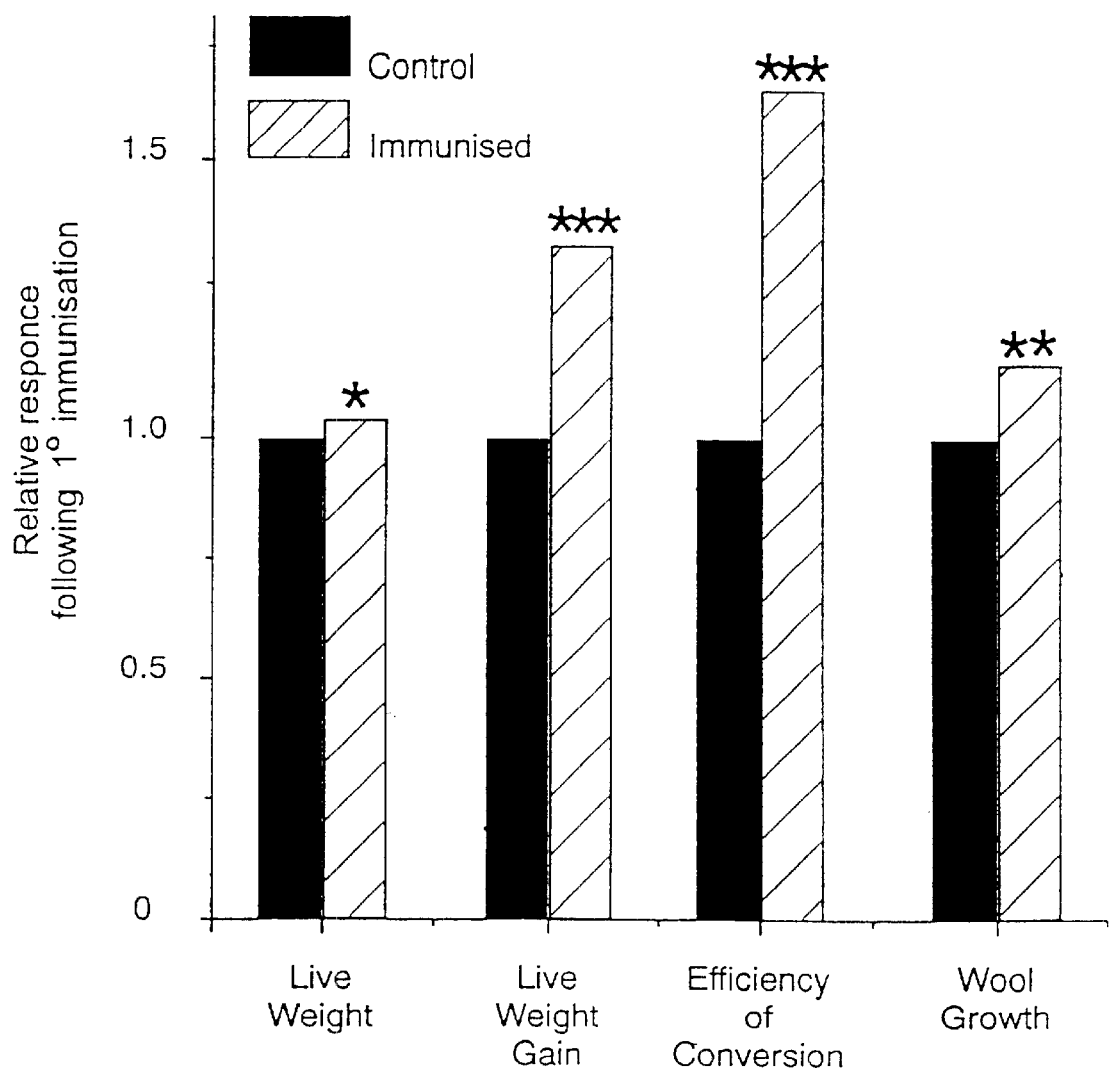
Figure 2C:
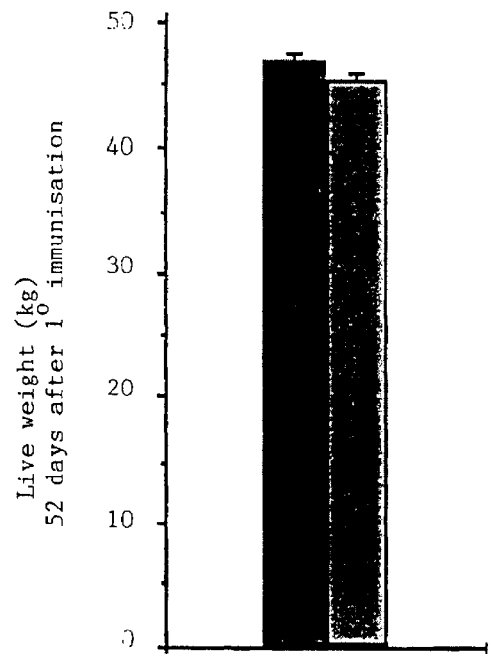
Figure 2D:
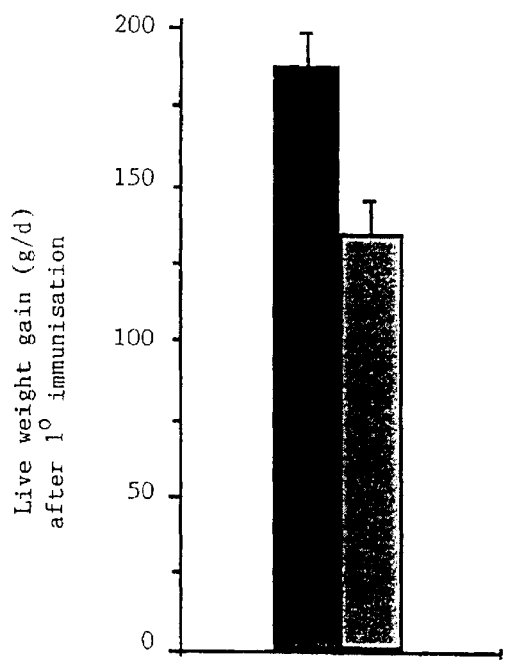
Figure 2E:
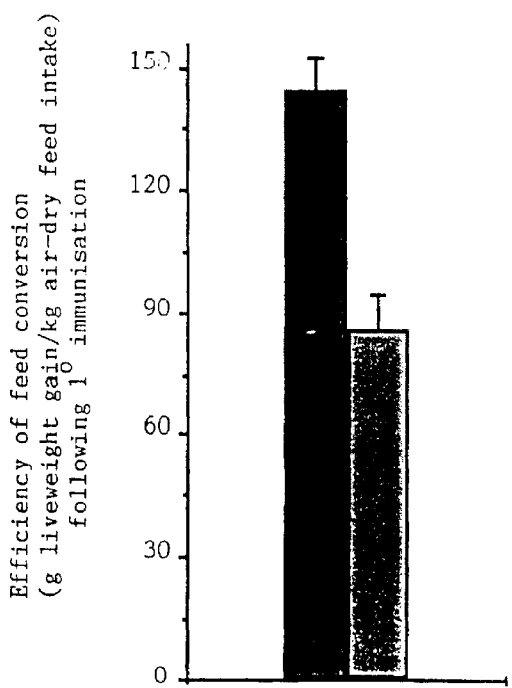
Figure 2F:
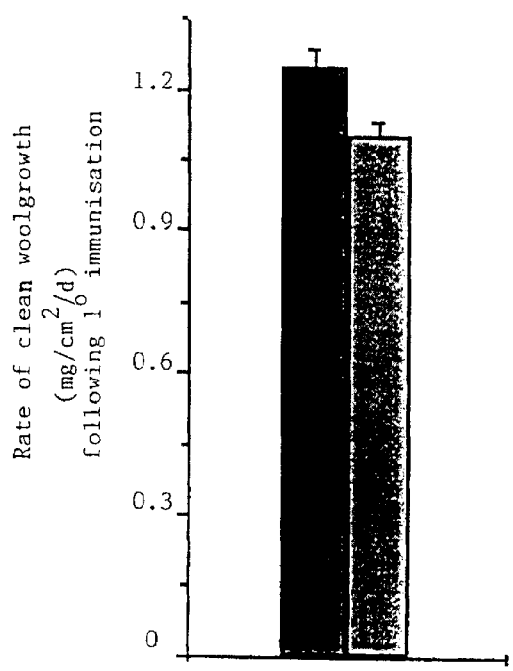

FIGS. 2A and 2B illustrate the response of the test animals subjected to the method of the invention when compared to control animals and shows the improved productivity of animals subjected to the invention. As with the first example FIG. 2B illustrates the same data as FIG. 2A after statistical analysis. FIGS. 2C–2F show the absolute values of the characteristics compared in FIG. 2B. It will be noted that the test animals exhibited improved liveweight, liveweight gain, efficiency of conversion and wool growth when compared to the control animals which did not receive the vaccine.

Figure 2H:
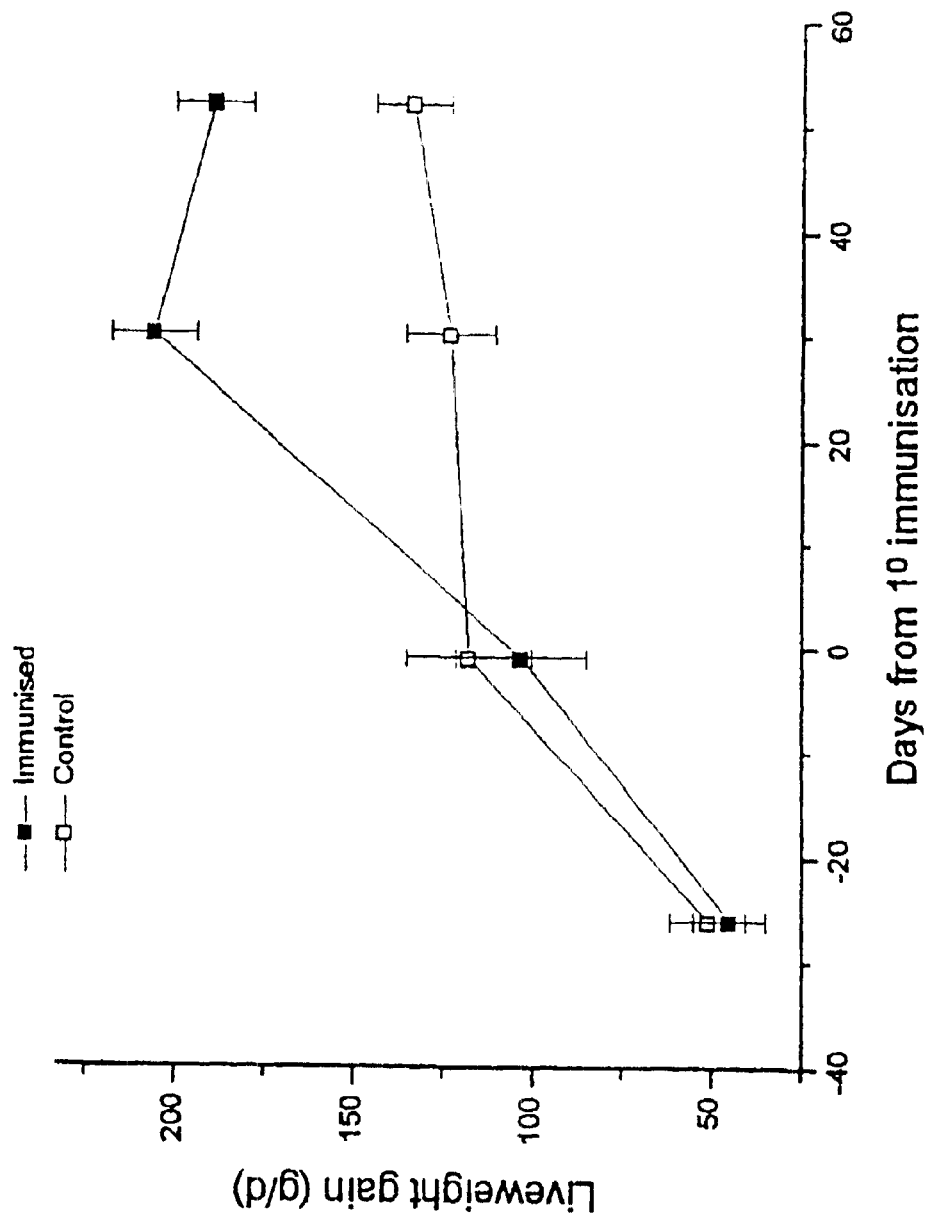

FIGS. 2G and 2H illustrate the course of change over time of liveweight and liveweight gain after the primary immunisation. The final points of the graphs contained in FIGS. 2G and 2H are the values represented in FIGS. 2B and 2C–2F.

EXAMPLE 3

Response in Grazing Weaner Wethers

The experiment was conducted using the following treatment groups:

Group I vaccine (antigen plus adjuvant);

Group II adjuvant alone (control); and

Group III phosphate-buffered saline (PBS) alone (control).

The vaccine was prepared using an antigen prepared from a washed preparation of mixed rumen protozoa separated from whole rumen contents using centrifugal elutriation (Munyard and Baker, 1994). The antigens in the vaccine were from rumen protozoa belonging to a number of genera including; Diploplastron, Eodinium, Polyplastron, Entodinium, Dasytrichia and Isotrichia and from the following methanogens; *Methanobrevibacter ruminatium* (strains M1 and Z6), *Methanosarcina barkeri* (strain M5) and three further strains of *Methanobrevibacter ruminatium* (strains SRF1, SRF2 and SRF3 (tentative identifications)).

14.5 mL fractions of whole cells (protozoal and bacterial) that had been fixed in formol saline (2.5% formaldehyde in 0.9% sodium chloride) ($10^6$ protozoal cells/mL and $10^9$ bacterial cells/mL) were incorporated with DEAE-dextran chloride into the vaccine as follows:

14.5 mL of the antigen preparation was washed in PBS (10 mM adjusted to pH 7.4, resuspended in 14.5 mL PBS containing diethylaminoethyl (DEAE)-dextran (10.8% w/v), and was mixed together with 1 mL of 12% (v/v in PBS) glycerol, 1 mL of 0.3% (v/v in PBS) Tween 80 and 13.5 mL squalene. The mix formed an emulsion containing oil droplets no larger than 40 $\mu$m in diameter. The dose administered was 1.5 mL per animal.

The vaccine (Group I), or the control injections of adjuvant alone (Group II) or of PBS alone (Group III) were administered intraperitoneally at the sublumbar fossa on the right mid-flank of the animal for the primary inoculation. The booster inoculation comprised $10^6$ protozoal cells and $10^8$ bacterial cells in 1.5 mL sterile PBS (Group I) or 1.5 mL sterile PBS alone (Groups II and III) administered subcutaneously 28 days after the primary inoculation.

The sheep grazed as a single group at the CSIRO Research Station, Yalanbee, at Bakers Hill, Western Australia from early autumn (March) to late spring (October). It will be appreciated that it is more difficult to establish a clear response when using grazing animals when compared to housed animals due to fluctuations in the amount and quality of feed intake and the presence of stressors in the environment that may confound the response.

Figure 3A:
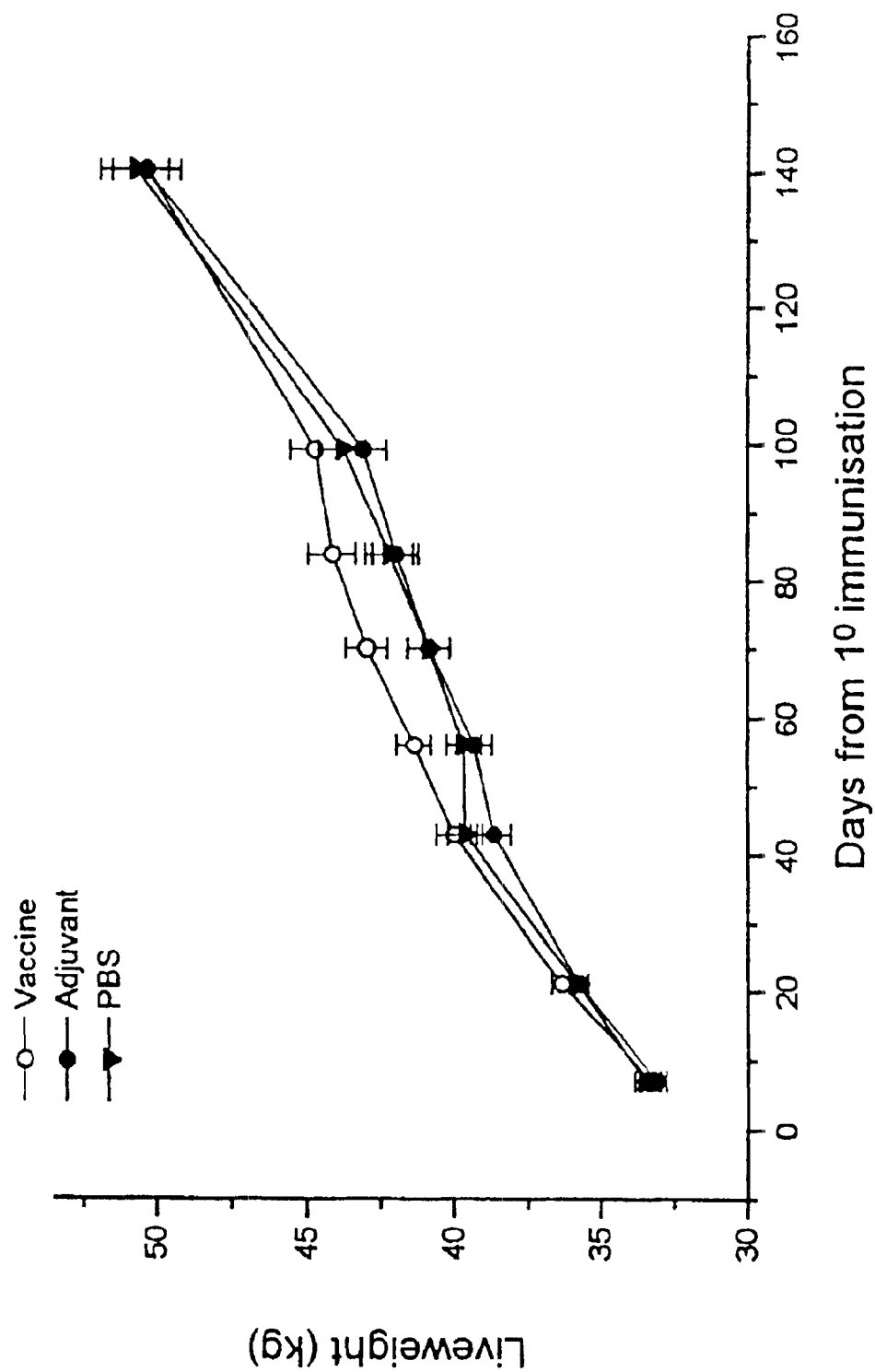
Figure 3B:
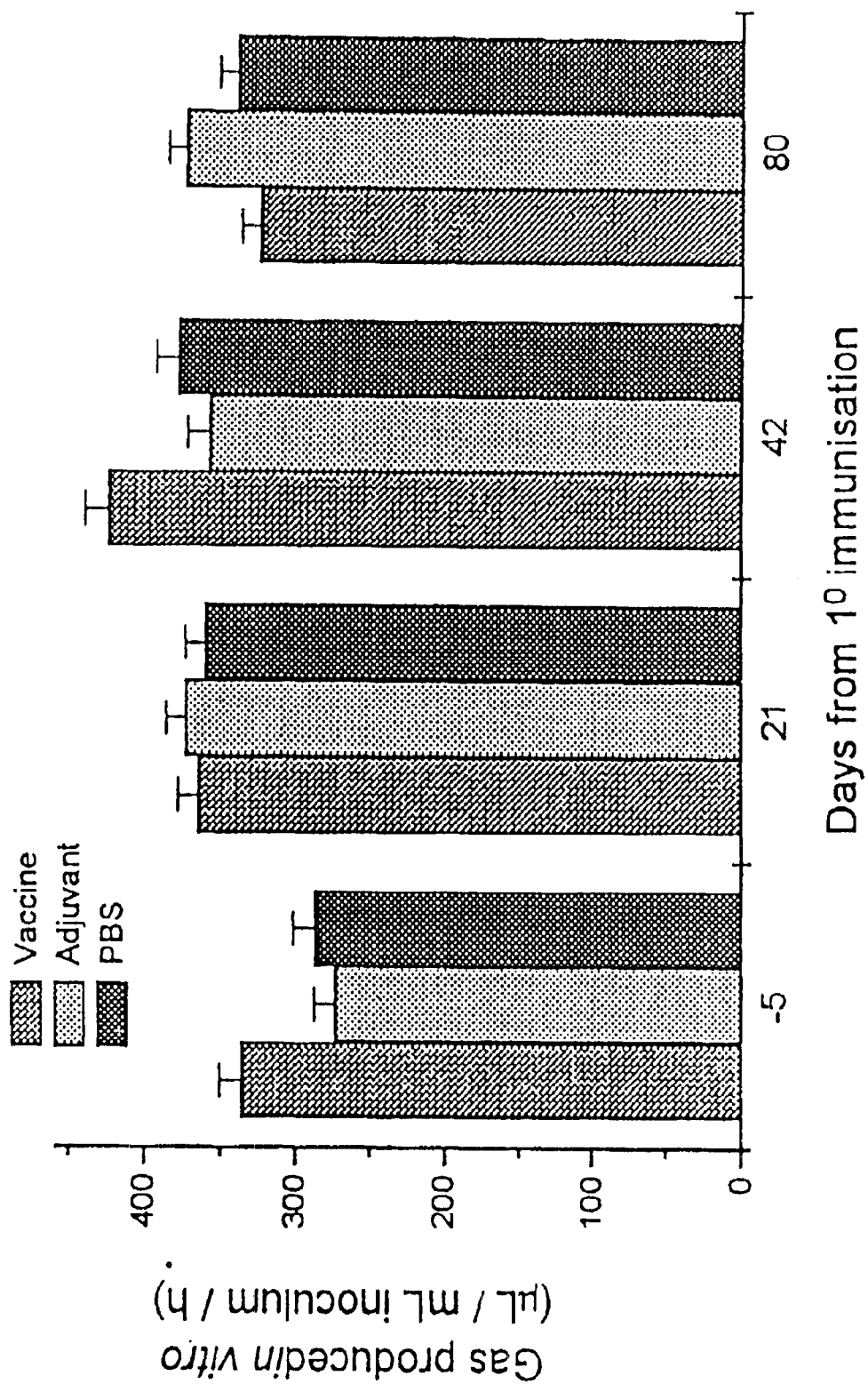

FIG. 3A illustrates the significantly increased liveweight of the animals to which the vaccine was administered compared with the control groups of animals. FIG. 3B illustrates an enhanced activity of the rumen microbial population by day 42 after the primary inoculation, as indicated by gas production by rumen contents incubated in vitro ($\mu$L gas produced/mL inoculum/h). This coincides with the enhanced liveweight response (FIG. 3A) and enhanced response in the rate of wool growth (FIG. 3C).

Figure 3D:
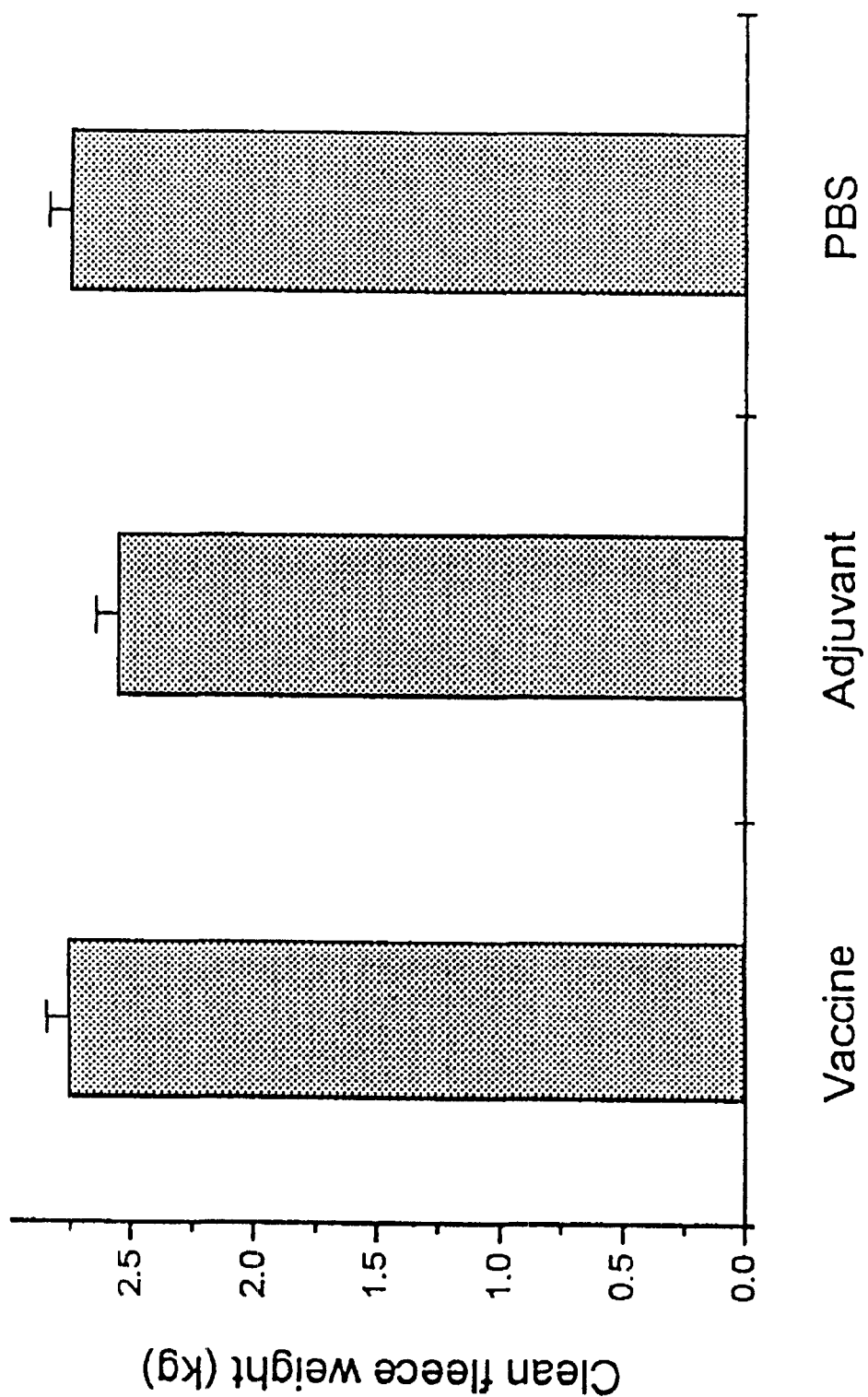

The weaners were shorn 61 days before the primary inoculation, and FIG. 3D illustrates a significantly improved clean fleece weight (kg) at shearing 145 days after primary inoculation in the group which received the vaccine (Group I), compared with the group which received adjuvant alone (Group II).

The improved clean fleece weight can be attributed to a significantly improved rate of wool growth (g clean wool/d), determined by dyebanding the wool, in the group that received the vaccine (Group I)(FIG. 3C).

There may be other aspects of the present invention, and modifications and variations thereto which will be apparent to one skilled in the art. All such aspects and modifications and variations are to be considered as incorporated within the scope of this invention.

The claims defining the invention are as follows:

1. A method of improving the live weight, live weight gain, efficiency of weight gain or wool growth of a ruminant animal, comprising administering to said animal an effective amount of an immunogenic preparation consisting essentially of rumen protozoa, a whole cell extract thereof, or both, wherein administration of said preparation increases IgG levels in the animal.

2. The method according to claim 1, wherein the rumen protozoa are of the order Entodiniomorphida.

3. The method according to claim 1, wherein the rumen protozoa are of the family Ophryoscolecidae.

4. The method according to claim 1, wherein the rumen protozoa are of the genus Entodinium.

5. The method according to claim 1, wherein the rumen protozoa are of the genus Polyplastron.

6. The method according to claim 1, wherein the rumen protozoa are of the genus Diploplastron.

7. The method according to claim 1, wherein the rumen protozoa are of the genus Eodinium.

8. The method according to claim 1, wherein the rumen protozoa are selected from the group consisting of orders Prostomatida, Trichostomatida, and Entodiniomorphida.

9. The method according to claim 1, wherein the rumen protozoa are selected from the group consisting of genera Diploplastron, Eodinium, Polyplastron, Entodinium, Dasytrichia, and Isotrichia.

10. The method according to claim 1, wherein the rumen protozoa have a cell size of approximately 10-100 $\mu$m, said cell size being the diameter of a sphere having a volume equal to the volume of the rumen protozoa.

11. The method according to claim 1, wherein the rumen protozoa have a cell size of approximately 5-200 $\mu$m, said cell size being the diameter of a sphere having a volume equal to the volume of the rumen protozoa.

12. A method according to claim 1 wherein the rumen protozoa are separated from whole rumen contents.

13. A method according to claim 1 wherein the immunogenic preparation further comprises at least one antigen from a methanogenic bacterium.

14. A method according to claim 1 wherein the immunogenic preparation further comprises a suitable adjuvant.

15. The method according to claim 14, wherein the adjuvant is DEAE-dextran chloride.

16. The method according to claim 14, wherein the adjuvant is Freund's complete adjuvant.

17. The method according to claim 14, wherein the adjuvant is Freund's incomplete adjuvant.

* * * * *